US005540669A

United States Patent [19]
Sage, Jr. et al.

[11] Patent Number: 5,540,669
[45] Date of Patent: Jul. 30, 1996

[54] IONTOPHORETIC DRUG DELIVERY SYSTEM AND METHOD FOR USING SAME

[75] Inventors: Burton H. Sage, Jr., Raleigh, N.C.; Ronald J. Flower, Vernon, N.J.

[73] Assignee: Becton, Dickinson and Company, Franklin Lakes, N.J.

[21] Appl. No.: 566,318

[22] Filed: Dec. 1, 1995

Related U.S. Application Data

[63] Continuation of Ser. No. 129,627, Sep. 30, 1993, abandoned.

[51] Int. Cl.$^6$ .................................................. A61N 1/30
[52] U.S. Cl. ............................................. 604/290; 604/20
[58] Field of Search ............... 604/20, 290; 607/149–152

[56] References Cited

U.S. PATENT DOCUMENTS

| | | | |
|---|---|---|---|
| 3,814,095 | 6/1974 | Lubens . | |
| 3,991,755 | 11/1976 | Vernon et al. | 604/20 |
| 4,141,359 | 2/1979 | Jacobson et al. | 604/20 |
| 4,211,222 | 7/1980 | Tapper . | |
| 4,340,047 | 7/1982 | Tapper et al. . | |
| 4,406,658 | 9/1983 | Lattin et al. . | |
| 4,456,012 | 6/1984 | Lattin . | |
| 4,764,164 | 8/1988 | Sasaki . | |
| 4,820,263 | 4/1989 | Spevak et al. . | |
| 4,927,408 | 5/1990 | Haak et al. . | |
| 4,950,229 | 8/1990 | Sage, Jr. | 604/20 |
| 5,084,008 | 1/1992 | Phipps . | |
| 5,088,977 | 2/1992 | Sibalis | 604/20 |
| 5,135,478 | 8/1992 | Sibalis | 604/20 |
| 5,160,316 | 11/1992 | Henley | 604/20 |
| 5,221,254 | 6/1993 | Phipps . | |
| 5,224,927 | 7/1993 | Tapper . | |
| 5,246,418 | 9/1993 | Haynes et al. | 604/20 |
| 5,256,137 | 10/1993 | Sage, Jr. | 604/20 |

*Primary Examiner*—John D. Yasko
*Assistant Examiner*—Mark Bockelman
*Attorney, Agent, or Firm*—Allen W. Wark

[57] ABSTRACT

An iontophoretic drug delivery device of the present invention includes a power source and an electrode assembly in electrical contact with at least three reservoirs, with at least two of the reservoirs containing an active formulation to be delivered to an applied area of a patient, with a switch for switching the flow of current from between the first electrode and the third electrode and between the second electrode and the first electrode so as to reduce sensation. The device also includes a timer for controlling the amount of time the electrical current flows between a pair of electrodes. In the preferred embodiment, the active formulation includes a local anesthetic such as Lidocaine and a vasoconstrictor such as Epinephrine. In this way, the device is suitable for use to deliver the local anesthetic to the applied area approximate the first reservoir for a first period of time and to deliver the local anesthetic to the applied area approximate the second reservoir during a second period of time. Thus, switching between pairs of electrodes and iontophoresing thereunder below the sensation threshold results in sensation anesthesia so that the current can be raised to deliver the drug without sensation.

8 Claims, 4 Drawing Sheets

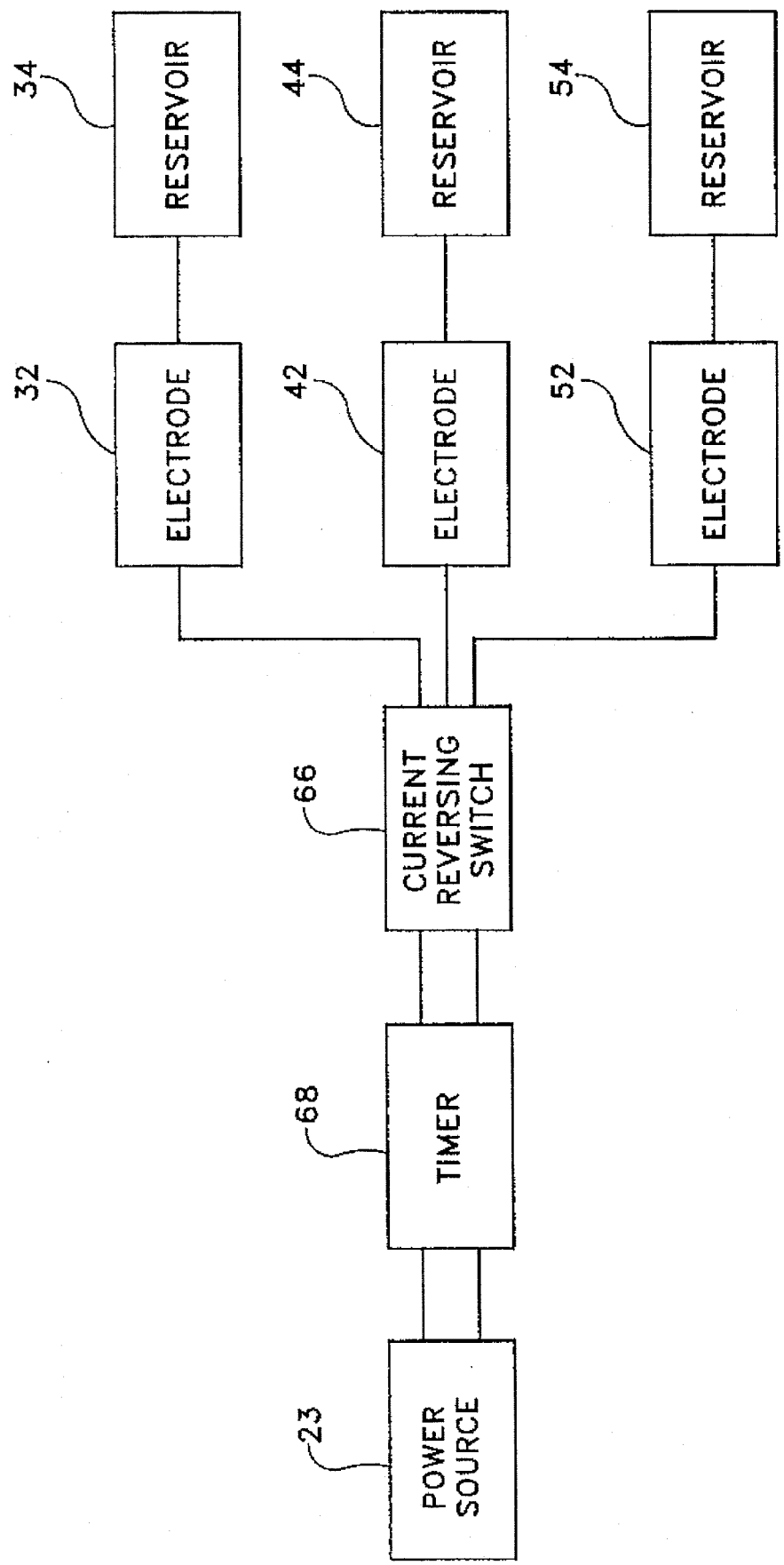

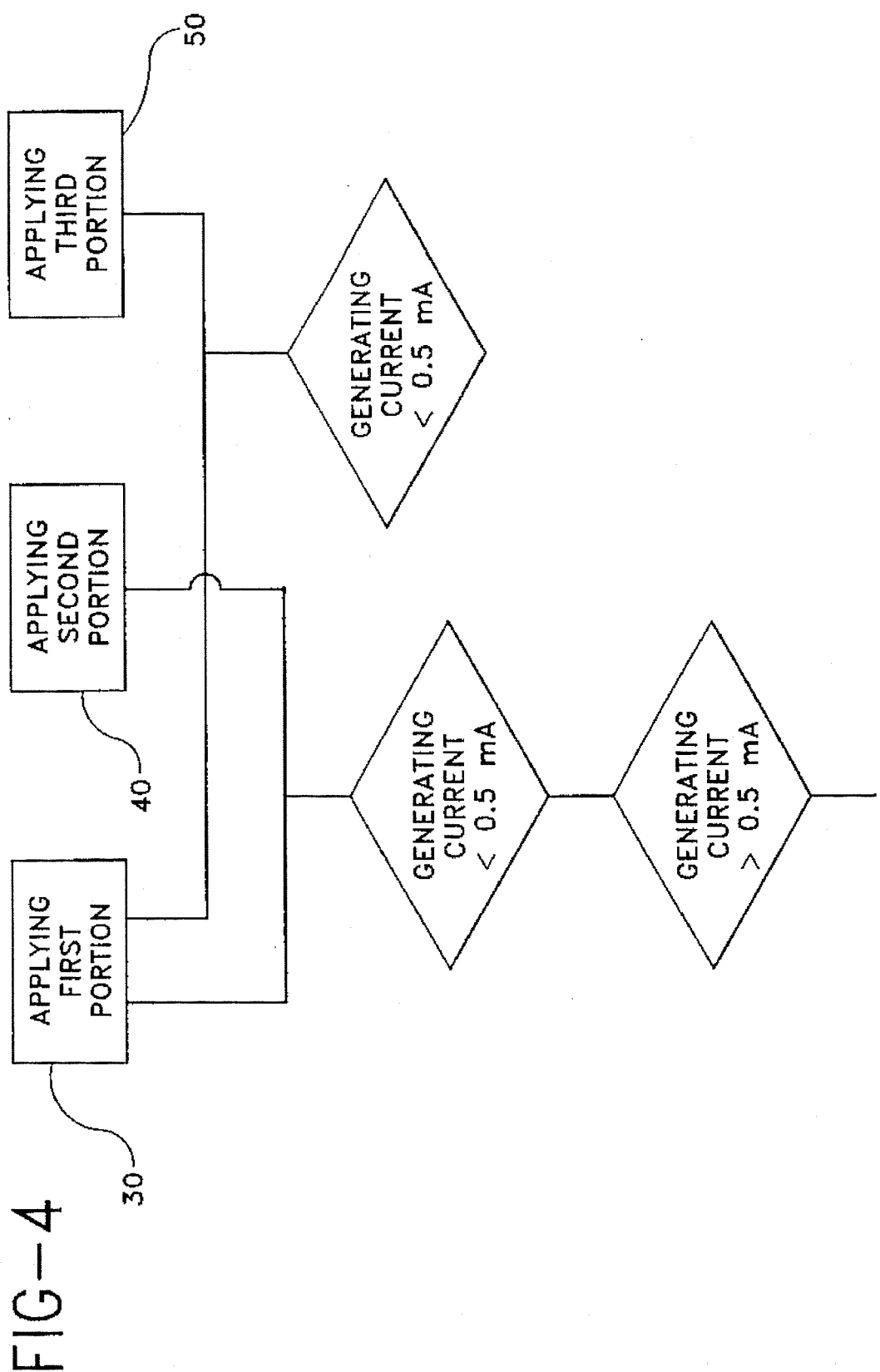

IONTOPHORETIC DRUG DELIVERY SYSTEM AND METHOD FOR USING SAME

This application is a continuation of application Ser. No. 08/129,627, filed Sep. 30, 1993, now abandoned.

FIELD OF THE INVENTION

The present invention generally relates to iontophoretic devices for delivering drugs or medicines to patients transdermally, i.e., through the skin, and more specifically relates to a drug delivery device with polarity switching for anesthetizing an area. In addition, the present invention relates to a method for anesthetizing an area using the iontophoretic drug delivering device.

BACKGROUND OF THE INVENTION

Transdermal drug delivery systems have, in recent years, become an increasingly important means of administering drugs. Such systems offer advantages clearly not achievable by other modes of administration such as avoiding introduction of the drug through the gastro-intestinal tract or punctures in the skin to name a few.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using iontophoresis, which according to Stedman's Medical Dictionary, is defined as "the introduction into the tissues, by means of an electric current, of the ions of a chosen medicament."

Conventional iontophoretic devices, such as those described in U.S. Pat. Nos. 4,820,263 (Spevak et al.), 4,927,408 (Haak et al.) and 5,084,008 (Phipps), the disclosures of which are hereby incorporated by reference, for delivering a drug or medicine transdermally through iontophoresis, basically consist of two electrodes, i.e., an anode and a cathode. Usually, electric current is driven from an external supply into the skin at the anode, and back out at the cathode. Accordingly, there has been considerable interest in iontophoresis to perform delivery of drugs for a variety of purposes.

However, several disadvantages and limitations have been associated with the use of such devices, including unacceptable levels of sensations due to current flow during iontophoresis, which in severe cases can be painful.

Attempts to reduce or mitigate such unacceptable levels of sensation have included employing materials between the electrode and the patient's skin as disclosed in U.S. Pat. No. 4,211,222 (Tapper), gradually imposing the current as disclosed in U.S. Pat. No. 4,340,047 (Tapper), pulsating the voltage as disclosed in U.S. Pat. No. 4,764,164 (Sasaki), reducing the current prior to switching polarity as disclosed in U.S. Pat. No. 4,406,658 (Lattin et al.), and alternating between biphasic stimulation and iontophoretic delivery as disclosed in U.S. Pat. No. 4,456,102 (Lattin), the disclosures of which are hereby incorporated by reference. Nevertheless, despite such attempts unacceptable sensation levels remain, especially when drug is delivered with high efficiency.

In addition to the above, amounts of a multivalent ion such as calcium, magnesium, phosphate and zinc have been included in the drug reservoir to reduce sensation as disclosed in U.S. Pat. No. 5,221,254 (Phipps), the disclosure of which is hereby incorporated by reference. However, the presence of such multivalent ions competes with the agent to be delivered and reduces the overall effect.

Specifically, unacceptable sensation levels have even been encountered during the iontophoretic delivery of local anesthetics, especially when rapid onset of the local anesthetic is desired involving, for example, the use of Novocaine, which is usually injected prior to dental work to relieve pain or the use of Lidocaine, which is usually applied as a topical, local anesthetic as disclosed in U.S. Pat. No. 4,950,229 (Sage, Jr. et al.), the disclosure of which is hereby incorporated by reference.

Thus, there has been a need for an iontophoretic drug delivery device, as well as a method for reducing skin pain, which would eliminate the problems and limitations associated with the prior devices discussed above, most significant of the problems being unacceptable levels of sensation. In addition, there has been a need for a device, which would reduce sensation without affecting the overall effect of the agent to be delivered.

SUMMARY OF THE INVENTION

In contrast to the prior devices discussed above, it has been found that a iontophoretic drug delivery device particularly suited for use in reducing or otherwise eliminating sensation can be constructed in accordance with the present invention. In addition, the device of the present invention does not compete with the agent(s) to be delivered, which for example in the case of skin pain relief, does not reduce the overall anesthesia.

The iontophoretic drug delivery device of the present invention for delivering at least one active agent to an applied area of a patient, such as the skin, mucous membrane and the like, includes power means for supplying a source of electrical current, electrode assembly means including at least three electrodes for driving the at least one active agent into the applied area of the patient along electrical field lines generated by the electrical current, a first reservoir situated in electrical communication with a first one of the electrodes and the first reservoir containing the at least one active agent to be delivered to the applied area of the patient, a second reservoir situated in electrical communication with a second one of the electrodes and the second reservoir containing the at least one active agent to be delivered to the applied area of the patient, a third reservoir situated in electrical communication with a third one of the electrodes, and means for switching the flow of the electrical current from between the first electrode and third electrode along the field lines during a first period of time and between the first electrode and the second electrode along electric field lines during a second period of time, so that the at least one active agent is delivered to the applied area of the patient approximate the first reservoir during the first period of time and the at least one active agent is delivered to the applied area of the patient approximate the second reservoir during the second period of time; wherein the current switching sequence may be repeated as desired.

In the preferred embodiment of the iontophoretic drug delivery device, the at least one active agent includes a local anesthetic and a vasoconstrictor, with the local anesthetic being Lidocaine and the vasoconstrictor being Epinephrine. In addition, the device includes timing means for controlling the means for switching the electrical current, with the timing means adapted so that the first and second time periods are preferably equal. The device also includes means for controlling the amount of electrical current.

The method of the present invention for reducing sensation during iontophoretically delivering at least one active agent to an applied area of a patient such as the skin, mucous membrane or the like, includes the steps of applying a first portion of an iontophoretic drug delivery device including an electrode assembly having a first electrode and a first reservoir containing at least one active agent to be delivered to the applied area of the patient, applying a second portion of the device including the electrode assembly having a second electrode and a second reservoir containing the at least one active agent to be delivered to the applied area of the patient, applying a third portion of the device including the electrode assembly having a third electrode and a third reservoir, generating an electrical current between the first electrode and the third electrode through the applied area of the patient during a first period of time so that the at least one active agent is delivered to the applied area of the patient approximate the first electrode and the first reservoir during the first period of time, and generating an electrical current between the first electrode and the second electrode through the applied area of the patient during a second period of time so that the at least one active agent is delivered to the applied area of the patient approximate the second electrode and the second reservoir during the second period of time.

In the preferred embodiment of the method of the present invention for reducing sensation, the at least one active agent includes a local anesthetic and a vasoconstrictor, with the local anesthetic being Lidocaine and the vasoconstrictor being Epinephrine. Also, the method includes the step of varying the period of time so that the first period of time is less than the second period of time and the step of varying the amount of electrical current. In addition, the step of generating an electrical current during the first period of time includes limiting the amount of electrical current delivered to at least initially less than or equal to 0.5 mA, and the step of generating electrical current during the second period of time includes limiting the amount of electrical current delivered to at least initially less than or equal to 0.5 mA. In addition, the method includes the step of generating an electrical current between the first electrode and the second electrode for at least one additional period of time during which the amount of electrical current delivered is greater than 0.5 mA, with the preferred range being approximately 0.05 mA to 1.5 mA.

The iontophoretic drug delivery device for delivering a local anesthetic formulation to an applied area of a patient, such as the skin, mucous membrane and the like, includes power means for supplying a source of electrical current, electrode assembly means including at least three electrodes for driving the local anesthetic formulation into the applied area of the patient along electrical field lines generated by the electrical current, a first reservoir situated in electrical communication with a first one of the electrodes and the first reservoir containing the local anesthetic formulation to be delivered to the applied area of the patient, a second reservoir situated in electrical communication with a second one of the electrodes and the second reservoir containing the local anesthetic formulation to be delivered to the applied area of the patient, a third reservoir situated in electrical communication with a third one of the electrodes, means for switching the flow of the electrical current between the first electrode and the third electrode along the field lines during a first period of time and between the first electrode and the second electrode along the field lines during a second period of time, so that the local anesthetic formulation is delivered to the applied area of the patient approximate the first electrode during the first period of time and the local anesthetic formulation is delivered to the applied area of the patient approximate the second electrode during the second period of time to eliminate unwanted sensation due to electrical current flowing through the applied area of the patient, and means for varying the amount of the electrical current and the amount of voltage.

In the preferred embodiment of the iontophoretic drug delivery device, the local anesthetic formulation includes a vasoconstrictor, with the local anesthetic formulation including Lidocaine and the vasoconstrictor being Epinephrine. In addition, the Lidocaine is in the range of 5% w/v–15% w/v and Epinephrine is in the range of 0.03% w/v–3.0% w/v.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIG. 3 is a block diagram depicting the various functions and components of the device of the present invention; and FIG. 4 is a block diagram depicting the various steps of the method of the present invention.

DETAILED DESCRIPTION OF THE PREFERRED EMBODIMENT

Figure 1:
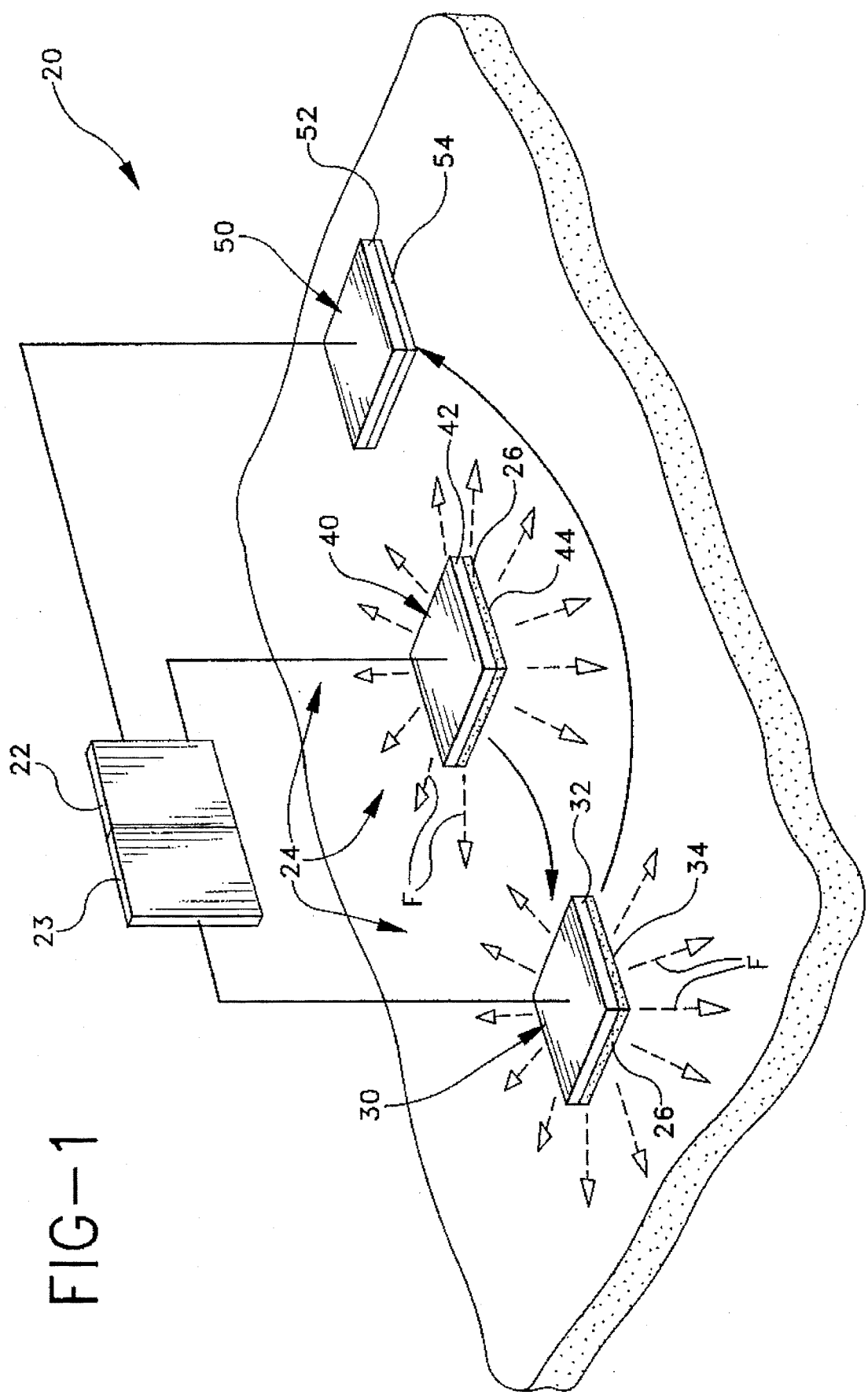
FIG. 1 is a schematic elevational view of the iontophoretic drug delivery device of the present invention illustrating connection of the electrode assembly to circuitry for driving the active ingredient into the skin of an animal.
Figure 2:
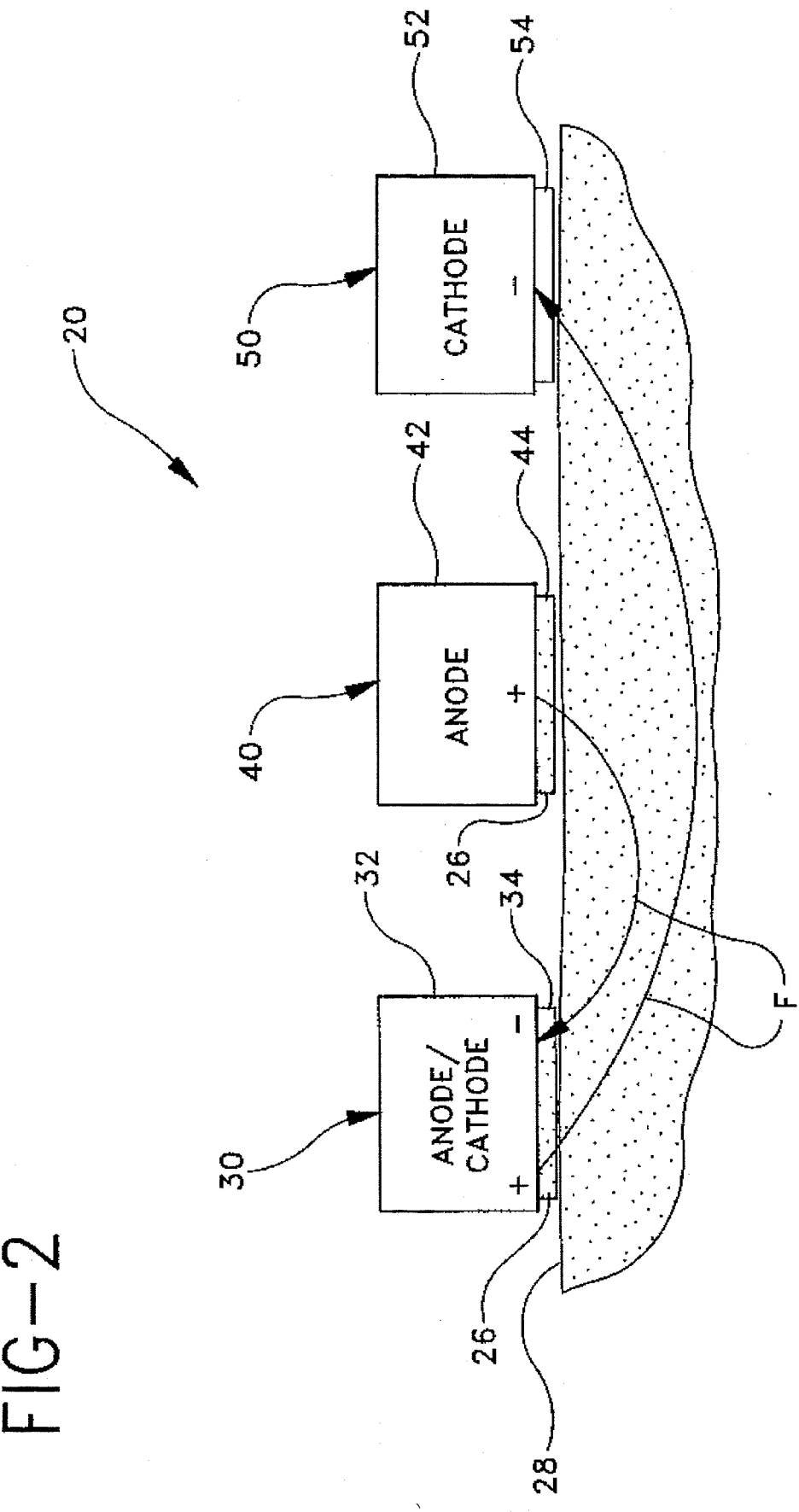
FIGS. 2 is a schematic, cross sectional view of the device of the present invention generally illustrated in FIG. 1 showing the direction of the current during delivery of the active ingredient.

The iontophoretic drug delivery system of the present invention is illustrated in FIGS. 1, 2, 3 and 4, with the device generally designated 20. Referring to FIGS. 1 or 2, the device 20 of the present invention includes a controller 22 and a power source 23 electrically connected to an electrode assembly 24 having three or more electrodes for establishing electric field lines F having lines of energy between the electrodes for use in delivering at least one active agent 26 iontophoretically to an applied area of the patient 28. It should be appreciated that the electrodes may be combined in the assembly 24 or separately provided as is well known in the art.

In the preferred embodiment, the electrode assembly is divided or otherwise separated into three portions, the first portion 30 includes the electrode 32 and the reservoir 34, with the reservoir being situated adjacent to and in electrical communication with the electrode, the second portion 40 also includes an electrode 42 and a reservoir 44, with the reservoir being situated adjacent to and in electrical communication with the electrode and the third portion 50 includes the electrode 52 and a reservoir 54, with the reservoir being situated adjacent to and in electrical communication with the electrode. In the preferred embodiment, both the first reservoir and the second reservoir 32 and 34 hold at least one active agent, formulation, medication or drug 26, preferably in an ionized or ionizable form, to be delivered iontophoretically to the applied area of the patient. However, all three electrodes 32, 42 and 52 may include an electrolyte, with the particular electrolyte not being essential to the present invention and merely a matter of choice. However, in this embodiment the electrolyte may include sodium chloride in an aqueous solution, matrix or the like, including water soluble polymer materials, with the polymer materials also including a structurally reinforcing member situated therein. In situations where a polymer material or another material is used, it may also act as an adhesive, eliminating the need in prior devices for an adhesive layer or the like.

Referring to FIGS. 1 or 3, the controller 22 and the power source 23, such as for example a battery, are connected in a circuit, with the controller 22 preferably including a microprocessor, a dc/dc converter to increase the battery supply to approximately 30 volts, a current regulator which is controlled by the microprocessor and a switch 66 for switching or otherwise directing the polarity or direction of the electrical current, and a timer 68 for monitoring the period of time the electrical current flows in a particular direction. In this way, the current flowing through the reservoirs 34, 44, 54 and the applied area 28 can be controlled with a compliance voltage sufficient to account for variations in skin impedance and losses within the reservoirs. In the preferred embodiment, the controller 22 includes means for controlling the level of current to be applied over time and also for varying the current. Accordingly, the device 20 can be utilized, for example, to vary the current $I_1$ during time period $T_1$, current $I_2$ during time period $T_2$, current $I_3$ during time period $T_3$, current $I_4$ during time period $T_4$, and current $I_5$ during time period $T_5$ and additional currents and time intervals as needed. Also, the controller may be adapted to include means for controlling the voltage V or the power I·V as well.

As is well known within the field, the device can be situated on the area of the patient to which the active agent is to be applied (the applied area) such as the skin and a voltage impressed across the electrodes 32, 42 or 44 of the electrode assembly 24 to cause electrical current to flow through the skin 28 of the patient to drive or otherwise transport the ionic active agent into the skin and the tissue along the field lines F to be absorbed by the body of the patient. The electric field lines F are sufficiently long, however, so that the active agent is transported to the desired depth within the skin, and possibly to the vasculature, to provide the desired effect, e.g., anesthetic, therapeutic or diagnostic. It should also be appreciated that the device of the present invention can be applied to other areas of the body such as mucous membranes depending upon the desired therapy and drugs to be delivered.

The active agent can have either a negative charge or a positive charge, but the active electrode must also be negatively or positively charged, respectively. Accordingly, as illustrated in FIGS. 1, 2 and 3, where the active agent contained in the reservoirs 34, 44 is positively charged, the electrical current flows from the first electrode 32 to the third electrode 52 during a first time period and the first electrode 32 acts as the active electrode and the third electrode 52 acts as the return electrode, with the drug 26 being delivered to the applied area of the skin approximate the first electrode 32 and first reservoir 34. After the elapse of a predetermined period of time ($T_1$), the flow of electrical current is switched so that it flows from the second electrode 42 through second reservoir 44 to the first electrode 32 during a second time period ($T_2$) in which the second electrode 42 acts as the active electrode and the first electrode 32 now acts as the return electrode. In this way, the active agent 26 is delivered to the applied area of the skin approximate the second electrode 42 and the second reservoir 44.

In the preferred embodiment, the device 20 of the present invention contains Lidocaine (a local anesthetic) and Epinephrine (a vasoconstrictor), which can be iontophoretically administered in as little as eight minutes utilizing up to approximately 1.5 mA of current with little if any sensation. Preferably, 15% (150 mgm/ML) of Lidocaine HCl (local anesthetic) and 45 μgm Epinephrine (vasoconstrictor), on a dry web may be used, with the Epinephrine being activated when the moisture from the reservoirs comes in contract with the web. In this way, the device can be used for anesthetizing the applied area as illustrated in FIG. 4 to minimize sensation from the insertion of a needle or the like. The Epinephrine can be utilized in combination with the Lidocaine to limit or otherwise restrict the Lidocaine formulation from being drawn away from the applied area by the vasculature, with the Epinephrine being deliverable first since it will also be positively charged and already in contact with the skin. However, it should be appreciated that the Lidocaine and the Epinephrine could be contained in the reservoirs in solutions.

As is readily apparent, when the Lidocaine is delivered through the cathode first at current levels less than 500 uA for a sufficient period of time, enough anesthetic will be delivered to deaden the nerves to subsequent higher currents. Accordingly, when the current is switched, the current can be increased to a much higher level with out the patient feeling much sensation. However, initially after switching the current, the current must again be kept at a level low enough and long enough at the true anode to allow the anesthetic to take effect, then the current can be increased to the level necessary to completely anesthetize the area under the anode. Most sensations produced by the ion flow into the cathode will be blocked by the small amount of anesthetic initially delivered under the cathode.

In addition, it should be appreciated that other formulations including Lidocaine HCl in the range of 5% w/v–15% w/v and Epinephrine in the range of 0.03% w/v–3.0% w/v may be utilized.

Active agent, drug, formulation, medication, medicament and active compound have been used herein to mean any pharmaceutical agent, such as therapeutic compounds, diagnostic agents, anesthetic agents and the like.

In addition, while the present invention has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals.

While the preferred embodiment of the present invention has been described so as to enable one skilled in the art to practice the device of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A method of reducing sensation during rapid iontophoretic delivery of at least a local anesthetic to an applied area of a patient such as the skin, mucous membrane or the like, comprising the steps of:

applying a first portion of an iontophoretic drug delivery device including an electrode assembly having a first electrode and a first reservoir containing the local anesthetic to be delivered to the applied area of the patient;

applying a second portion of the device including said electrode assembly having a second electrode and a second reservoir containing said local anesthetic to be delivered to the applied area of the patient;

applying a third portion of the device including said electrode assembly having a third electrode and a third reservoir;

generating an electrical current between said first electrode and said third electrode through the applied area of the patient during a first period of time at low current so that at least enough of said local anesthetic is delivered to the applied area of the patient approximate said first electrode and said first reservoir during said first period of time to anesthetize the applied area approximate said first electrode and said first reservoir at least sufficiently to avoid sensation due electrical current flowing through the applied area of the patient approximate thereto; and generating an electrical current between said first electrode and said second electrode through the applied area of the patient during a second period of time so that during said second period of time a higher current is provided for a longer period of time to said second electrode to deliver said local anesthetic to anesthetize the applied area of the patient approximate said second electrode and said second reservoir without unwanted sensation due to electrical current flowing through the applied area of the patient and to minimize sensation from the subsequent insertion of a needle or the like into the applied area of the patient.

2. A method of reducing sensation as defined in claim 1, wherein a vasoconstrictor is delivered along with said local anesthetic.

3. A method of reducing sensation as defined in claim 2, wherein said local anesthetic is Lidocaine and said vasoconstrictor is Epinephrine.

4. A method of reducing sensation as defined in claim 1, further comprising the step of varying the amount of electrical current.

5. A method of reducing sensation as defined in claim 1, wherein said step of generating an electrical current during said first period of time includes limiting the amount of electrical current delivered to at least initially less than or equal to 0.5 mA.

6. A method of reducing sensation as defined in claim 5, wherein said step of generating electrical current during said second period of time includes limiting the amount of electrical current delivered to at least initially less than or equal to 0.5 mA.

7. A method of reducing sensation as defined in claim 6, further comprising the step of generating an electrical current between said first electrode and said second electrode for at least one additional period of time during which the amount of electrical current delivered is greater than 0.5 mA.

8. A method of reducing sensation as defined in claim 7, wherein the amount of electrical current delivered during said at least one additional period of time is in the range of approximately 0.05 mA to 1.5 mA.

\* \* \* \* \*